(12) United States Patent
Chan (10) Patent No.: US 8,252,290 B2
(45) Date of Patent: Aug. 28, 2012

(54) HERBAL COMPOSITION FOR TREATMENT OF INSOMNIA AND OTHER RELATED DISORDERS AND A METHOD OF PREPARING THE SAME

(75) Inventor: Hei Ling Helen Chan, Hong Kong (HK)

(73) Assignee: Vita Green Health Products Company Limited

( * ) Notice: Subject to any disclaimer, the term of this patent is extended or adjusted under 35 U.S.C. 154(b) by 885 days.

(21) Appl. No.: 12/041,674

(22) Filed: Mar. 4, 2008

(65) Prior Publication Data

US 2009/0226482 A1  Sep. 10, 2009

(51) Int. Cl.
*A61K 36/06* (2006.01)
*A61K 36/09* (2006.01)
(52) U.S. Cl. .................................. 424/195.15
(58) Field of Classification Search .......... None
See application file for complete search history.

(56) References Cited

U.S. PATENT DOCUMENTS 6,245,360 B1 *  6/2001  Markowitz .................... 424/641

FOREIGN PATENT DOCUMENTS

DE   10053155 A1 *  5/2002
EP    1331007 A2 *  7/2003

* cited by examiner

*Primary Examiner* — Amy L Clark
(74) *Attorney, Agent, or Firm* — Eagle IP Limited; Jacqueline C. Lui (57) ABSTRACT

An herbal composition comprises an extract of *Radix Rehmanniae*, and an extract of *Poria, Ganoderma Lucidum, Semen Ziziphi Spinosae, Semen Platycladi, Radix Rehmanniae Praeparata, Radix Angelicae Sinensis, Radix Et Rhizoma Salviae Miltiorrhizae, Rhizoma Chuanxiong, Rhizoma Atractylodis Macrocephalae, Fructus Gardeniae, Cortex Moutan, Radix Bupleuri, Radix Paeoniae Alba, Rhizoma Cyperi, Pericarpium Citri Reticulatae, Fructus Aurantii, Radix Glycyrrhizae*, and *Os Draconis*. The herbal composition is prepared by separately extracting *Radix Rehmanniae*, and the remaining herbs. The composition is suitable for treatment of insomnia and other related disorders.

17 Claims, 6 Drawing Sheets

HERBAL COMPOSITION FOR TREATMENT OF INSOMNIA AND OTHER RELATED DISORDERS AND A METHOD OF PREPARING THE SAME

FIELD OF INVENTION

This invention relates to an herbal composition and in particular a composition for treatment of insomnia and other related disorders. This invention also relates to methods of preparing such herbal composition.

BACKGROUND OF INVENTION

Insomnia is a type of sleeping disorders in which insomniacs find it difficult or are incapable of sleeping and/or maintaining their sleep for a reasonable period of time with frequent awakenings. Psychological instabilities, such as fear, stress and anxiety, are believed to be the main reasons leading to insomnia, although regular intake of certain medications or caffeine also causes insomniacs' failure to attain good quality sleep.

Medication and behavioral therapy are popular remedies for insomnia, and a combination of these therapies is often practiced to increase the efficacy of the treatment. Sleeping pills such as benzodiazepines (e.g. temazepam and diazepam) and non-benzodiazepine prescription drugs are commonly used as treatment, but adverse effects, such as psychological and physical dependence on hypnotics and neurological, physiological, and cognitive disturbances, as well as withdrawal symptoms on cessation of medication, may accompany the use of these drugs.

SUMMARY OF INVENTION

The present invention relates to an herbal composition, which is also presented as a composition further comprising a pharmaceutically acceptable carrier or vehicle.

One aspect of the present invention provides an herbal composition comprising a mixture of at least a first extract and a second extract, in which the first extract comprises a purified extract of the herb *Radix Rehmanniae*, and a second extract comprises the extracts of the herbs *Poria, Ganoderma Lucidum, Semen Ziziphi Spinosae, Semen Platycladi, Radix Rehmanniae Praeparata, Radix Angelicae Sinensis, Radix Et Rhizoma Salviae Miltiorrhizae, Rhizoma Chuanxiong, Rhizoma Atractylodis Macrocephalae, Fructus Gardeniae, Cortex Moutan, Radix Bupleuri, Radix Paeoniae Alba, Rhizoma Cyperi, Pericarpium Citri Reticulatae, Fructus Aurantii, Radix Glycyrrhizae*, and *Os Draconis*.

The herbal composition of the invention is obtained by a process comprising obtaining the first extract described above, obtaining the second extract also described above, and mixing the first extract and the second extract to obtain the herbal composition of the invention, wherein the first extract and the second extract are separately extracted and purified.

The herbal composition in accordance with this invention is suitable to be administrated for the treatment of insomnia or other sleep-related disorders or phobia, general anxiety disorder, anxiety-related disorders, or alleviating withdrawal symptoms of sleeping pills.

DETAILED DESCRIPTION OF THE PREFERRED EMBODIMENTS

As used herein and in the claims, "comprising" means including the following elements but not excluding others. The process of "boiling" refers to the process of heating the herbs with water to a high temperature, generally at about 100° C.± about 5° C. The process of "simmering" or "decocting" refers to heating the herbs with water and keeping the heated content at temperatures between 90° C. and 100° C.

The term "heatiness" refers to heat disharmony which refers to a body condition caused either by external factors or internal deficiencies, resulting in signs and symptoms such as red face, fever, dislike of heat, preference of cold for reducing discomfort, rapid movement, hot temper, thirst or desire for cold drinks, dark urine and oliguria, dry stool and constipation.

The present invention relates to an herbal composition for treatment of insomnia and other related disorders.

One aspect of the present invention provides an herbal composition comprising a mixture of at least a first extract and a second extract, in which the first extract comprises a purified extract of the herb *Radix Rehmanniae*, and the second extract comprises the extracts of the herbs *Poria, Ganoderma Lucidum, Semen Ziziphi Spinosae, Semen Platycladi, Radix Rehmanniae Praeparata, Radix Angelicae Sinensis, Radix Et Rhizoma Salviae Miltiorrhizae, Rhizoma Chuanxiong, Rhizoma Atractylodis Macrocephalae, Fructus Gardeniae, Cortex Moutan, Radix Bupleuri, Radix Paeoniae Alba, Rhizoma Cyperi, Pericarpium Citri Reticulatae, Fructus Aurantii, Radix Glycyrrhizae*, and *Os Draconis*.

In one embodiment, the herbal composition further comprises a pharmaceutically acceptable carrier or vehicle. In another preferred embodiment, the herbal composition provided is in powder form, incapsulated form, in the form of a drink. The herbal composition of the present invention may also be in the form of a nutritional supplement such as but not limited to powder or liquid such as but not limited to milk, soup, food additives, sports drinks, sweetened oral tablet/candy, or chocolate format In another embodiment of the present invention, the composition of the herbal composition of the instant patent is listed in Table 2 wherein the ingredients in the composition are in such an amount that it provides the highest efficacy for treatment of insomnia or sleeping disorders.

In yet another embodiment, the herbal composition of the invention is obtained by a process comprising obtaining the first extract described above by extracting the herb *Radix Rehmanniae* with an aqueous solution, obtaining the second extract also described above by extracting an herbal mixture of *Poria, Ganoderma Lucidum, Semen Ziziphi Spinosae, Semen Platycladi, Radix Rehmanniae Praeparata, Radix Angelicae Sinensis, Radix Et Rhizoma Salviae Miltiorrhizae, Rhizoma Chuanxiong, Rhizoma Atractylodis Macrocephalae, Fructus Gardeniae, Cortex Moutan, Radix Bupleuri, Radix Paeoniae Alba, Rhizoma Cyperi, Pericarpium Citri Reticulatae, Fructus Aurantii, Radix Glycyrrhizae*, and *Os Draconis* with an aqueous solution, and mixing the first extract and the second extract to obtain the herbal composition of the invention, wherein the first extract and the second extract are separately extracted and purified.

According to another aspect of the present invention, a method is provided for preparing the herbal composition with the ingredients described above which comprises obtaining a first extract comprising an extract of *Radix Rehmanniae*; obtaining a second extract comprising extracts of the herbs of *Poria, Ganoderma Lucidum, Semen Ziziphi Spinosae, Semen Platycladi, Radix Rehmanniae Praeparata, Radix Angelicae Sinensis, Radix Et Rhizoma Salviae Miltiorrhizae, Rhizoma Chuanxiong, Rhizoma Atractylodis Macrocephalae, Fructus Gardeniae, Cortex Moutan, Radix Bupleuri, Radix Paeoniae Alba, Rhizoma Cyperi, Pericarpium Citri Reticulatae, Fructus Aurantii, Radix Glycyrrhizae*, and *Os Draconis*; and mixing the first extract and the second extract to form a composition suitable as an oral formulation; the first extract and the second extract are separately extracted and purified prior to their mixing. In a non-limiting embodiment, the first extract comprises a water extract of *Radix Rehmanniae*.

In one implementation, the preparatory method further comprises a first step of extracting *Radix Rehmanniae* with an aqueous solution, e.g. water, and concentrating, purifying, and drying the extract to obtain a concentrated, purified, and dried first extract.

In the next step, the second extract is obtained by extracting the herb *Os Draconis* with an aqueous solution, e.g. water, followed by extracting an herbal mixture of *Poria, Ganoderma Lucidum, Semen Ziziphi Spinosae, Semen Platycladi, Radix Rehmanniae Praeparata, Radix Angelicae Sinensis, Radix Et Rhizoma Salviae Miltiorrhizae, Rhizoma Chuanxiong, Rhizoma Atractylodis Macrocephalae, Fructus Gardeniae, Cortex Moutan, Radix Bupleuri, Radix Paeoniae Alba, Rhizoma Cyperi, Pericarpium Citri Reticulatae, Fructus Aurantii*, and *Radix Glycyrrhizae* with an alcohol, e.g. ethanol. Then, these two extracts are mixed, concentrated, and dried to produce the second extract.

Afterwards, the first and second extracts are mixed with a pharmaceutical carrier in the last step of the method, and the thus produced pharmaceutical mixture is packaged in the form of an oral formulation. In one embodiment, the pharmaceutical carrier is starch.

The present invention has shown that the herb unprepared or raw *Radix Rehmanniae* exhibits the functions of clearing the kidney heat (清肾热), replenishing the yin vacuity (清阴热), and alleviating the intestine heat (清肠热) by replenishing yin fluid when used in the composition according to the present invention. According to what the inventor has discovered, *Radix Rehmanniae* present in the herbal composition can be separately extracted and purified before being mixed with the other herbs to preserve its active ingredients; thus, all the three aforesaid functions, especially the function of removing the intestine heat (清肠热), was thus retained in the instant herbal composition. Consequently, the herbal composition according to the instant invention helps in clearing heat (清热), creates less constipation problems among patients, and minimizes aforesaid side effects.

Another aspect of the present invention is that patients taking the herbal composition of the instant invention have experienced good results in achieving reduced insomnia faster because their yin fluids are replenished quickly.

The present invention provides an herbal composition with ingredients of one specific embodiment listed in Table 1 below by medicinal name, corresponding processed form, common name, related herbs, and alternative names.

TABLE 1

| | Medicinal Name | Processed Form | Common Name | Related herb(s) | Alternative Name |
|---|---|---|---|---|---|
| 1. | Radix Rehmanniae (生地) | Radix Rehmanniae Praeparata (熟地/熟地黄) | Radix Rehmanniae (地黄) | — | Radix Rehmanniae (鲜地黄 / 牛地黄 / 干地黄) |
| 2. | Poria (茯苓) | — | Poria (茯苓) | Sclerotium Poriae Circum Radicem Pini (茯神) | Poria (杜茯苓 / 松苓 / 茯苓皮) |
| 3. | Ganoderma Lucidum (靈芝) | — | Lingzhi (靈芝) | — | Ganoderma Lucidum (赤芝 / 木靈芝 / 靈芝草 / 紅芝 / 瑞草) |
| 4. | Semen Ziziphi Spinosae (酸枣仁) | Semen Ziziphi Spinosae (stir-baked) (炒酸枣仁) | Semen Ziziphi Spinosae (酸枣仁) | — | Semen Ziziphi Spinosae (枣仁 / 川枣仁 / 山枣仁 / 棘子) |
| 5. | Semen Platycladi (柏子仁) | Semen Platycladi (frost-like powder) (柏子仁霜) | Semen Platycladi (柏子仁) | — | Semen Platycladi (香柏 / 扁柏 / 柏子 / 柏仁) |
| 6. | Radix Rehmanniae Praeparata (熟地黄) | Radix Rehmanniae Praeparata (熟地 / 熟地黄) | Radix Rehmanniae Praeparata (熟地) | Radix Rehmanniae (生地) | Radix Rehmanniae Praeparata (熟地 / 伏地) |
| 7. | Radix Angelicae Sinensis (當歸) | — | Radix Angelicae (當歸) | — | Radix Angelicae (秦歸 / 雲歸) |

TABLE 1-continued

| | Medicinal Name | Processed Form | Common Name | Related herb(s) | Alternative Name |
|---|---|---|---|---|---|
| 8. | Radix Et Rhizoma Salviae Miltiorrhizae (丹参) | — | Radix Et Rhizoma Salviae Miltiorrhizae (丹参) | — | Radix Et Rhizoma Salviae Miltiorrhizae (紅参 / 血参 / 赤参 / 紫丹参) |
| 9. | Rhizoma Chuanxiong (川芎) | — | Rhizoma Chuanxiong (川芎) | — | Rhizoma Chuanxiong (芎 / 小葉川芎) |
| 10. | Rhizoma Atractylodis Macrocephalae (白朮) | Rhizoma Atractylodis Macrocephalae (Processed with terra/bran) (土白朮/ 炒白朮) | Rhizoma Atractylodis Macrocephalae (白朮) | — | Rhizoma Atractylodis Macrocephalae (于朮/ 于白朮) |
| 11. | Fructus Gardeniae (梔子) | Fructus Gardeniae Praeparatus (焦梔子) | Fructus Gardeniae (梔子) | Gardenia jasminoides Ellis (梔子葉 / 梔子花根 / 梔子花) Itoa orientalis Hemsl (梔子皮) | Fructus Gardeniae (黃梔子 / 山梔 / 山黃枝 / 水橫枝 / 山枝子) |
| 12. | Cortex Moutan (丹皮) | — | Cortex Moutan (牡丹皮) | — | Cortex Moutan (粉丹皮 / 木芍藥 / 洛陽花 / 牡丹根皮) |
| 13. | Radix Bupleuri (柴胡) | Radix Bupleuri (炙柴胡/ 醋柴胡 / 鱉血柴胡) | Radix Bupleuri (柴胡) | — | Radix Bupleuri (南柴胡 / 北柴胡) |
| 14. | Radix Paeoniae Alba (白芍) | Radix Paeoniae Alba (炒白芍 / 酒白芍) | Radix Paeoniae Alba (白芍) | Radix Paeoniae Rubra (赤芍) | Radix Paeoniae Alba (芍藥 / 杭芍 / 毫芍 / 川芍) |
| 15. | Rhizoma Cyperi (香附) | Rhizoma Cyperi (Processed with vinegar) (醋香附) | Rhizoma Cyperi (香附) | — | Rhizoma Cyperi (生香附 / 莎草 / 大香附) |
| 16. | Pericarpium Citri Reticulatae (陳皮) | — | Pericarpium Citri Reticulatae (陳皮) | — | Pericarpium Citri Reticulatae (橘皮 / 廣陳皮 / 桔皮) |
| 17. | Fructus Aurantii (枳殼) | Fructus Aurantii (麩炒枳殼) | Fructus Aurantii (枳殼) | Fructus Aurantii Immaturus (枳實) | Fructus Aurantii (只殼 / 枸橘 / 枳 / 野橘丁 / 臭橘 / 蘇橘;) |
| 18. | *Radix Et. Rhizoma Glycyrrhizae (甘草) | Radix Et. Rhizoma Glycyrrhizae Praeparata Cum Melle (炙甘草 / 蜜甘草) | Radix Et. Rhizoma Et. Rhizoma Glycyrrhizae (粉甘草) | — | Radix Et. Rhizoma Glycyrrhizae (甜草 / 甜根子 / 粉甘草 / 生甘草) |
| 19. | **Os Draconis (生龍骨) | Os Draconis (calcined) (煆龍骨) | Os Draconis (龍骨) | Dens Draconis (龍齒及炮製品) | — |

The individual components in the composition according to the present invention and as used in the claims are generally referred by the medicinal names of the herbs (Column 2, Table 1) as the working embodiment, but the processed form (Column 3, Table 1) and the related herbs (Column 5, Table 1) may be used as substitutes or equivalents***. The information shown in Table 1 was extracted from the Pharmacopoeia of the People's Republic of China 2005.

(* The name in ingredient 18, *Radix Et. Rhizoma Glycyrrhizae*, is taken from the 2005 edition of the Pharmacopoeia of the People's Republic of China. Ingredient 18 has an alternative name of *Radix Glycyrrhizae* in the older version(s) of the Pharmacopoeia of the People's Republic of China.)

(** The information of ingredient 19, *Os Draconis*, is taken from older versions of the Pharmacopoeia of the People's Republic of China.)

(*** For ingredient 1, *Radix Rehmanniae*, and ingredient 6 *Radix Rehmanniae Praeparata*, their respective processed form and related herbs cannot be used as substitutes or equivalents.)

In one embodiment, the composition of the herbal composition uses the medicinal herbs shown in Column 2, Table 1, and is also listed in Table 2 below.

TABLE 2

| No. | Herb | Composition (g) | By weight % |
|---|---|---|---|
| 1 | Radix Rehmanniae | 44 | 10 |
| 2 | Poria | 21 | 5 |
| 3 | Ganoderma Lucidum | 21 | 5 |
| 4 | Semen Ziziphi Spinosae | 18 | 5 |
| 5 | Semen Platycladi | 18 | 5 |
| 6 | Radix Rehmanniae Praeparata | 18 | 5 |
| 7 | Radix Angelicae Sinensis | 19 | 5 |
| 8 | Radix Et Rhizoma Salviae Miltiorrhizae | 18 | 5 |
| 9 | Rhizoma Chuanxiong | 9 | 2 |
| 10 | Rhizoma Atractylodis Macrocephalae | 9 | 2 |
| 11 | Fructus Gardeniae | 14 | 4 |
| 12 | Cortex Moutan | 18 | 5 |
| 13 | Radix Bupleuri | 14 | 4 |
| 14 | Radix Paeoniae Alba | 18 | 5 |
| 15 | Rhizoma Cyperi | 18 | 5 |
| 16 | Pericarpium Citri Reticulatae | 14 | 4 |
| 17 | Fructus Aurantii | 18 | 5 |
| 18 | Radix Glycyrrhizae | 14 | 4 |
| 19 | Os Draconis | 21 | 5 |
| 20 | Starch | 44 | 10 |
| | Total | 388 | 100 |

In yet another embodiment of the present invention, the composition of the herbal composition using the medicinal herbs shown in Column 2, Table 1 can also be in ranges as listed in Examples 1 and 2 of Table 3 below.

TABLE 3

| No. | Herb | Example 1 Weight % | Example 2 Weight % |
|---|---|---|---|
| 1 | Radix Rehmanniae | 5-15 | 9-12 |
| 2 | Poria | 3-10 | 4-8 |
| 3 | Ganoderma Lucidum | 3-10 | 4-8 |
| 4 | Semen Ziziphi Spinosae | 2-8 | 3-6 |
| 5 | Semen Platycladi | 2-8 | 3-6 |
| 6 | Radix Rehmanniae Praeparata | 2-8 | 3-6 |
| 7 | Radix Angelicae Sinensis | 2-8 | 3-6 |
| 8 | Radix Et Rhizoma Salviae Miltiorrhizae | 2-8 | 3-6 |
| 9 | Rhizoma Chuanxiong | 1-5 | 1-4 |
| 10 | Rhizoma Atractylodis Macrocephalae | 1-5 | 1-4 |
| 11 | Fructus Gardeniae | 1-6 | 2-5 |
| 12 | Cortex Moutan | 2-8 | 3-6 |
| 13 | Radix Bupleuri | 1-6 | 2-5 |
| 14 | Radix Paeoniae Alba | 2-8 | 3-6 |
| 15 | Rhizoma Cyperi | 2-8 | 3-6 |
| 16 | Pericarpium Citri Reticulatae | 1-6 | 2-5 |
| 17 | Fructus Aurantii | 2-8 | 3-6 |
| 18 | Radix Glycyrrhizae | 1-6 | 2-5 |
| 19 | Os Draconis | 3-10 | 4-8 |
| 20 | Starch | 5-15 | 9-12 |

Figure 1:
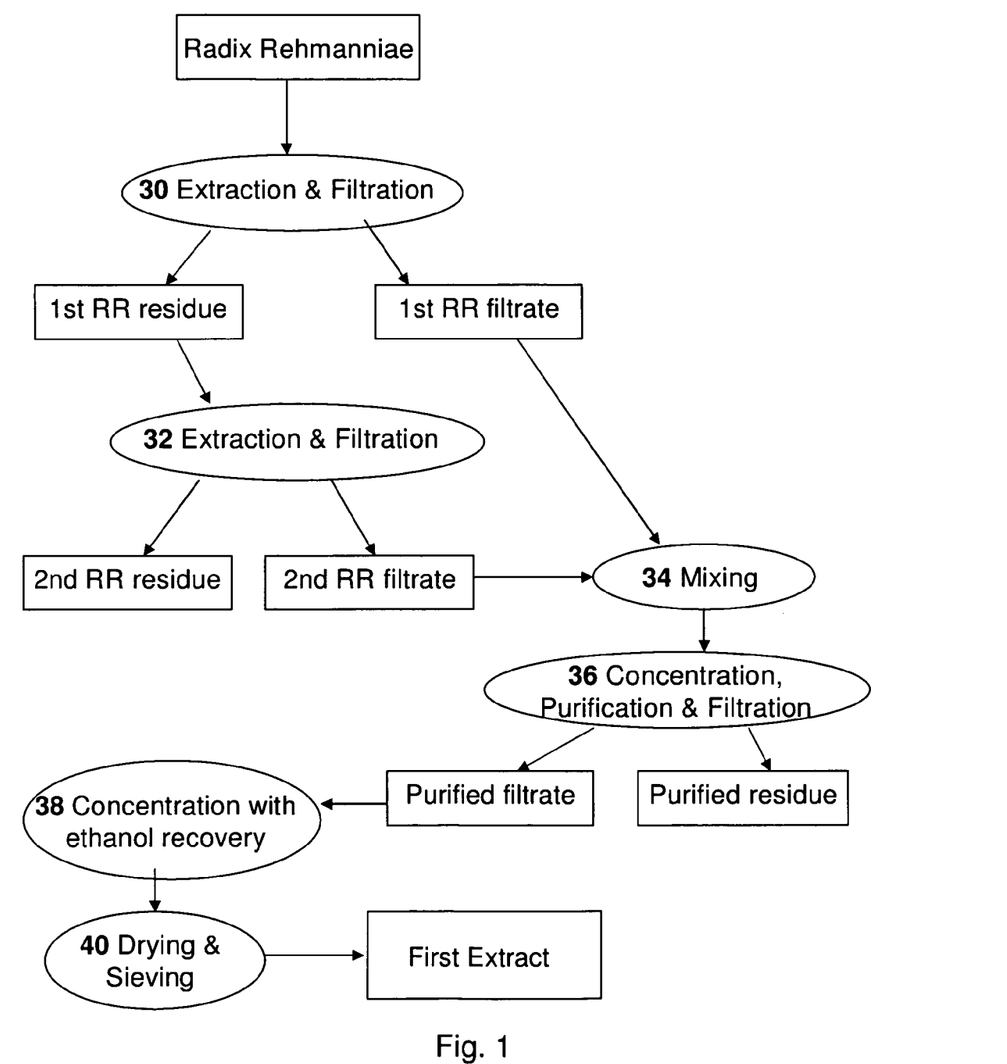
FIGS. 1, 2 and 3 provide outlines of the overall process for preparing the herbal composition suitable for the treatment of insomnia and other related disorders according to one embodiment of the present invention.
Figure 2:
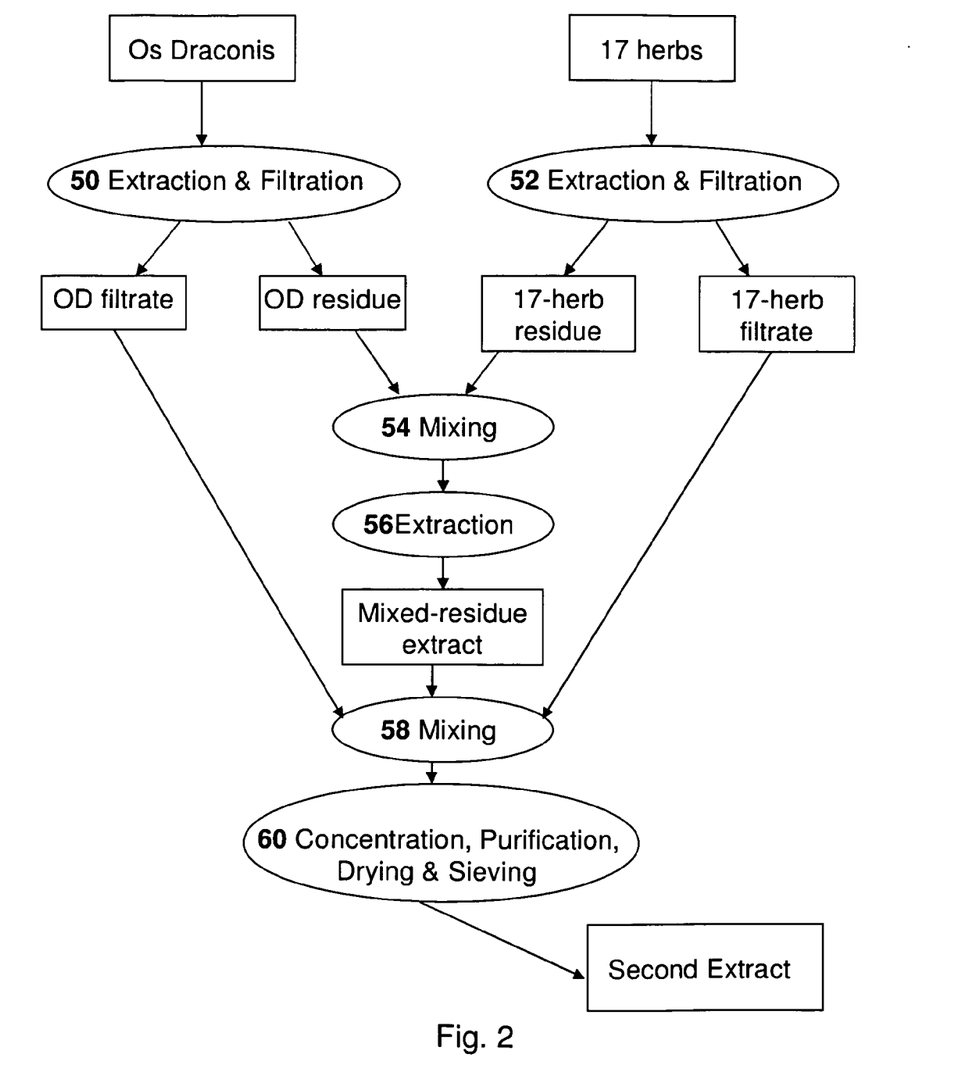
Figure 3:
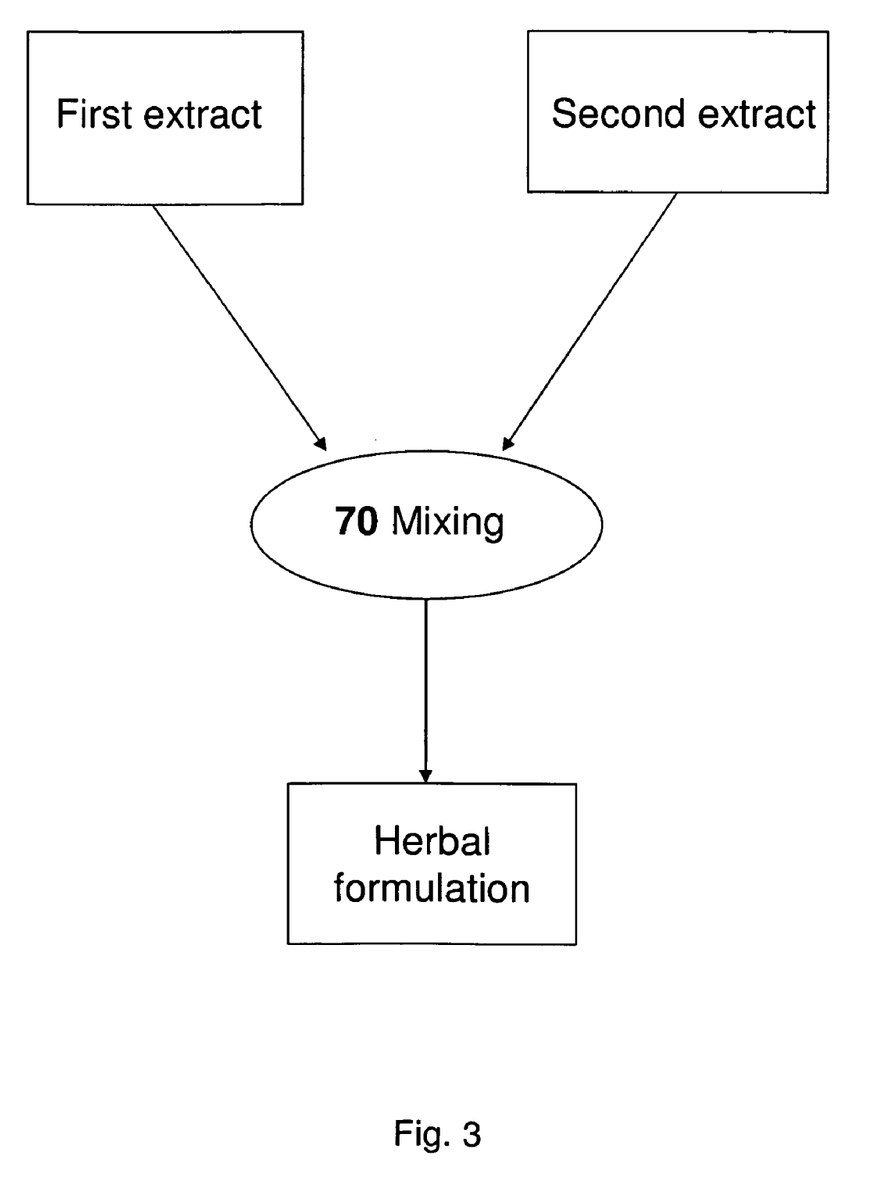

FIGS. 1, 2 and 3 outline the major steps for preparing the herbal composition according to the present invention. The following is one specific example of preparing the herbal composition according to the instant invention.

Referring first to FIG. 1, the steps for extracting the purified extracts of *Radix Rehmanniae* (First Extract) were provided. In an initial extraction and filtration step 30, powders of *Radix Rehmanniae* were first put into a percolator and soaked in about six volumes of water for 2 hours, and the mixture was then simmered and extracted (under circulation in every 15 minutes) for 2 hours. The extracted mixture was filtered to obtain a first *Radix Rehmanniae* filtrate ($1^{st}$ RR filtrate in FIG. 1), and a first *Radix Rehmanniae* residue ($1^{st}$ RR residue in FIG. 1).

Afterwards, the first Radix Rehmanniae residue was extracted (step 32) in which the residue was heated in five volumes of water, simmered and extracted (under circulation in every 15 minutes) for one hour. The resulting mixture was filtered (step 32) and the thus obtained filtrate ($2^{nd}$ RR filtrate in FIG. 1) was mixed (step 34) with the first *Radix Rehmanniae* filtrate.

The mixed filtrate was concentrated (step 36) under reduced pressure as a moist paste with a relative density of about 1.10 (at 60° C. to 70° C.). The moist paste was purified by ethanol precipitation (step 36) in which ethanol was slowly added to the moist paste under stirring until the ethanol concentration of the aqueous mixture became about 60%. The resulting aqueous mixture was settled for 24 hours and filtered into a purified filtrate and a purified residue (step 36).

The purified filtrate was concentrated under reduced pressure (step 38) to recover ethanol and a concentrated paste having a relative density between 1.20 and 1.25. The concentrated paste was dried and processed into powders by spray drying (step 40) with an inlet temperature of 200° C. to 220° C. and an outlet temperature of 80° C. to 100° C. Afterwards, the dried powders were passed through an 80 mesh sieve (step 40) to obtain fine powders of purified extract of *Radix Rehmanniae* (as First Extract in FIGS. 1 and 3).

Turning now to FIG. 2, the steps for obtaining an extract of herbs of *Poria, Ganoderma Lucidum, Semen Ziziphi Spinosae, Semen Platycladi, Radix Rehmanniae Praeparata, Radix Angelicae Sinensis, Radix Et Rhizoma Salviae Miltiorrhizae, Rhizoma Chuanxiong, Rhizoma Atractylodis Macrocephalae, Fructus Gardeniae, Cortex Moutan, Radix Bupleuri, Radix Paeoniae Alba, Rhizoma Cyperi, Pericarpium Citri Reticulatae, Fructus Aurantii, Radix Glycyrrhizae*, and *Os Draconis* were provided. Powders of *Os Draconis* were put into a jacketed kettle and heated (step 50) with four volumes of water for two hours. The heated mixture was then cooled to room temperature and filtered (step 50) through a 300-mesh filter cloth to obtain an *Os Draconis* filtrate (OD filtrate in FIG. 2), and an *Os Draconis* residue (OD residue in FIG. 2).

The 17 remaining herbs (*Poria, Ganoderma Lucidum, Semen Ziziphi Spinosae, Semen Platycladi, Radix Rehmanniae Praeparata, Radix Angelicae Sinensis, Radix Et Rhizoma Salviae Miltiorrhizae, Rhizoma Chuanxiong, Rhizoma Atractylodis Macrocephalae, Fructus Gardeniae, Cortex Moutan, Radix Bupleuri, Radix Paeoniae Alba, Rhizoma Cyperi, Pericarpium Citri Reticulatae, Fructus Aurantii*, and *Radix Glycyrrhizae*) were extracted (step 52) in ethanol (four times the weight of these 17 herbs) in the following manner: one third of these herbs were first dissolved in approximately half of the total volume of ethanol used in an extraction tank and pressed flat, followed by the addition of the remaining two thirds of the herbs as well as the remaining ethanol with stirring for 10 minutes. Upon immersion for at least 12 hours, the ethanol mixture was heated by steam with a pressure of 0.1 MPa to 0.2 MPa (under circulation in every 10 minutes). When the temperature of the ethanol mixture reached 50° C. to 60° C., the inlet valve of the cooler for the cooling water and condenser was opened. Heating was then continued and the ethanol mixture was extracted (under circulation in every 15 minutes with reflux for 5 minutes) at a temperature of 75° C. to 85° C. for two hours. The extracted mixture was then filtered (step 52) into a 17-herb filtrate and a 17-herb residue.

Afterwards, the *Os Draconis* residue (from step 50) and the 17-herb residue (from step 52) were mixed (step 54) and extracted (step 56) with water at least twice to obtain the mixed-residue extract. Each of the extractions 56 was performed as follows. The two residues were first heated with three volumes of water by steam with a pressure of 0.1 MPa to 0.2 MPa in an extraction tank. When the temperature of the mixture reached 50° C. to 60° C., the inlet valve of the cooler for the cooling water and condenser was opened. Then, heating was continued and the mixture was extracted (under circulation in every 15 minutes with reflux for 5 minutes) at a temperature of 75° C. to 85° C. for two hours.

Finally, the *Os Draconis* filtrate from step 50, the 17-herb filtrate from step 52, and the mixed-residue extract from step 56 were all mixed (step 58). The filtrate mixture was concentrated, followed by ethanol recovery to result in a concentrated paste having a relative density between 1.18 and 1.21 (tested at 55° C. to 65° C.). The concentrated paste was dried into powders by spray drying with a preheat temperature of 60° C. to 70° C., an inlet temperature of 170° C. to 180° C., and an outlet temperature of 80° C. to 90° C. Finally, the dried powders were passed through an 80 mesh sieve (step 60) to obtain the dried powders of Second Extract (step 60).

As illustrated in FIG. 3, powders of the First Extract and powders of the Second Extract 2 were mixed (step 70) together with a pharmaceutical carrier inside a pharmaceutical blender for 30 minutes to form the final product of the herbal composition. In one embodiment, the pharmaceutical carrier is starch.

The present invention is further defined by the following examples, which are not intended to limit the present invention.

Example 3

Thin Layer Chromatography on Purified Extract of Radix Rehmanniae using Catalpol as Marker Since catalpol (represented by formula I) can be used as a marker for *Radix Rehmanniae*, it is used in this analysis to verify whether the purified extract (the First Extract) produced by the steps illustrated in FIG. 1 is a *Radix Rehmanniae* extract.

Formula I

Catalpol

Preparation of Specimen

One gram of the sample tested (i.e. the purified extract of *Radix Rehmanniae* produced according to the steps illustrated in FIG. 1) was first added to 20 mL methanol and the methanol mixture was then extracted under reflux in water bath for 2 hours. The extract was then cooled for filtration. The filtrate was evaporated to remove all the water therein, and the dried filtrate residue was dissolved in 10 mL water and extracted three times with 15 mL 1-butanol for each extraction. Upon completion, the extract was mixed with the 1-butanol layer with the addition of 1.5 g activated carbon. The mixture was then well-shaken and settled for 2 minutes before filtration. After the filtrate was evaporated to remove all the water therein, the dried filtrate residue was further dissolved in 2 mL ethanol and the resulting solution was used as the specimen.

Preparation of Control

A 0.5 mg/1 mL catalpol solution in methanol was used as control.

Analysis

Thin Layer Chromatography (TLC) was performed with reference to The Pharmacopoeia of the People's Republic of China 2005, Volume I, Appendix VI B as follows. 2 µL of each of the specimen and the control were dotted on a thin plate of Silica Gel G and developed using trichloromethane:methanol:water (14:6:1) as the mobile phase. Upon drying, anisaldehyde was added to the plate and stained. The stained plate was then heated at 105° C. until the spots could be clearly observed.

Figure 4:
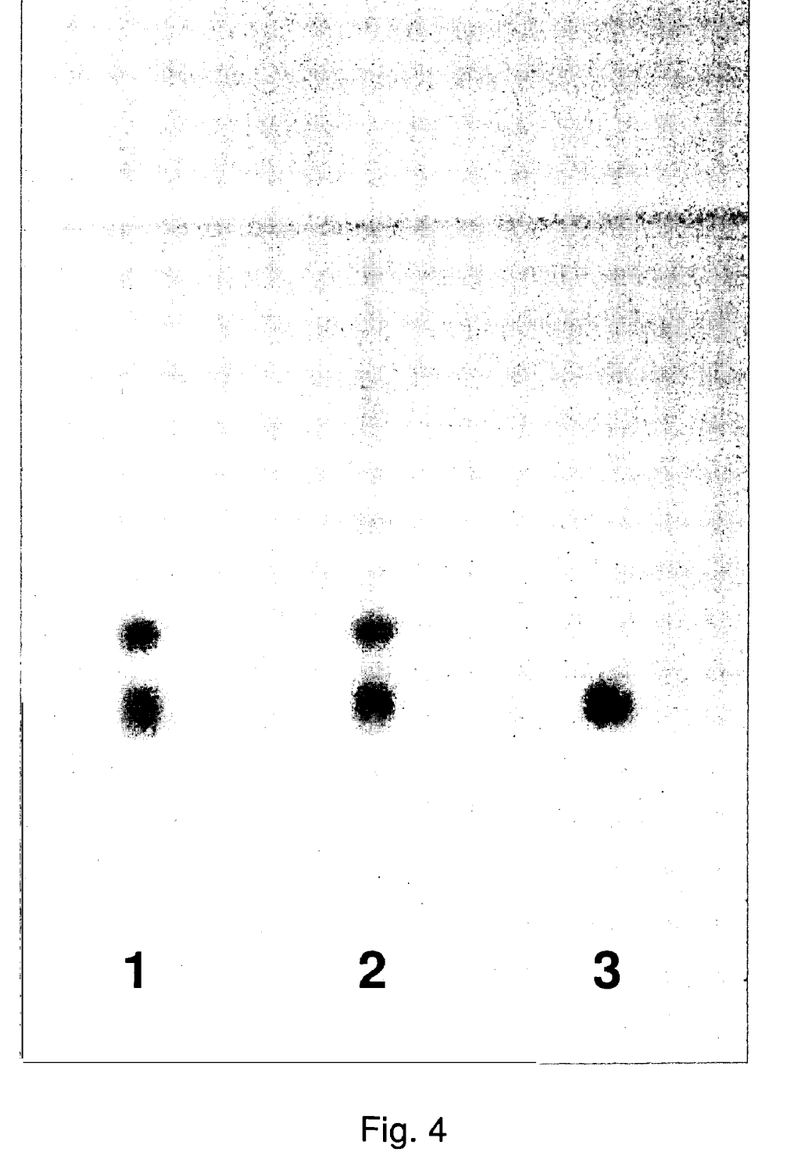
FIG. 4 is an image of a thin layer chromatography plate after developing the purified extract of *Radix Rehmanniae* with trichloromethane:methanol:water (14:6:1) under heating at 105° C.

The result is shown in FIG. 4 in which the specimen (numbered as 1 and 2) and the control (numbered as 3) were dotted on the silica plate. It may be observed that the specimen had identical spot as that from the control at the relevant position on the silica plate, verifying that the sample tested was *Radix Rehmanniae*.

Example 4

HPLC Analysis on Purified Extract of Radix Rehmanniae using Catalpol as Marker

This High Performance Liquid Chromatography (HPLC) analysis is performed with reference to The Pharmacopoeia of the People's Republic of China 2000, Volume I, Appendix VI D.

Preparation of Specimen 0.2 g of the sample tested (i.e. the purified extract of *Radix Rehmanniae* produced according to the steps illustrated in FIG. 1) was heated with 25 mL methanol under reflux in a conical flask for two hours. Upon cooling, additional methanol was added to the mixture to replenish the loss of methanol from heating, and the resulting mixture was well-shaken before filtration. 10 mL of the filtrate was evaporated to remove all the water therein, and the dried filtrate residue was dissolved and diluted with a solution of acetonitrile-0.1% phosphoric acid (1:99) to a total volume of 100 mL. The diluted solution was then filtered with a micropore filter (0.45 µL) to obtain the filtrate as the specimen.

Preparation of Control

A 20 µg/1 mL catalpol solution in acetonitrile-0.1% phosphoric acid (1:99) was used as the control.

Analysis

Figure 5:
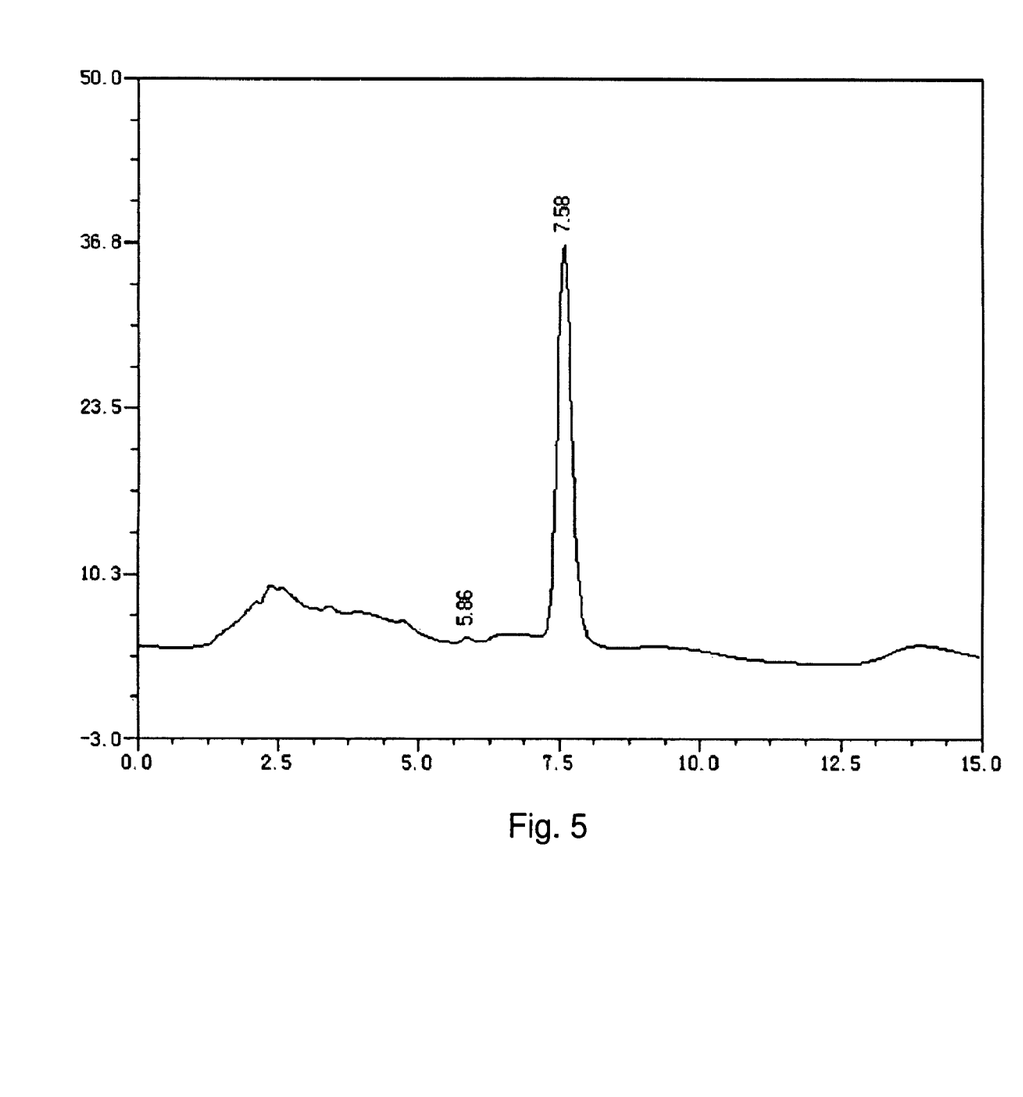
FIGS. 5 and 6 are HPLC spectrum for catalpol and for the purified extract of *Radix Rehmanniae* respectively.
Figure 6:
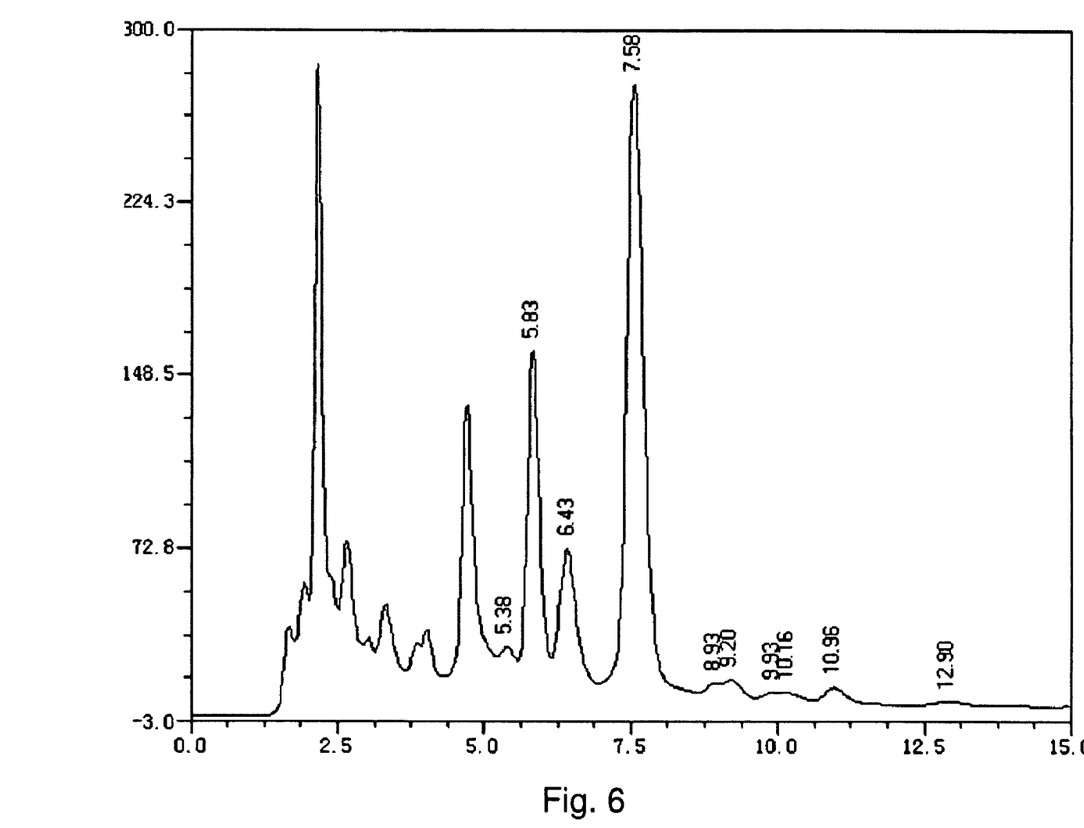

The content of catalpol present in the specimen was measured in which 10 µL of each of the specimen and the control were added to the HPLC apparatus. From FIGS. 5 & 6, peak at 7.58 minutes (corresponding to catalpol) was observed in both the specimen and control spectrum, indicating that catalpol was present in the specimen.

Example 5

Clinical Observations of Patients Treated with Herbal Composition (of Table 2)

There were five patients taking part in this study who suffered from insomnia, anxiety, or anxiety depression. The particulars for the patients and the corresponding treatments are listed in Table 4 below.

TABLE 4

| No. | Patient particulars | Treatment |
|---|---|---|
| 1 | Male; 46 years old | Patient complained of not being able to sleep at night for 2 months and waking up at 3 am even if he was able to fall asleep. After taking the herbal composition at a dosage of 2 capsules at 8 p.m. nightly for 10 days, he was able to fall asleep but woke up at 4 a.m. in the morning. He was then given another capsule of the herbal composition at 4 a.m. to treat the early wakening and he responded. The patient was maintained thereafter for 10 months on 2 capsules nightly. There were no complaints of heatiness. |
| 2 | Female; 36 years old | Patient suffering from anxiety depression on antidepressants complained of insomnia. She was given the herbal composition at 2 capsules nightly, responded well in 2 weeks and was maintained since. There were no complaints of heatiness. |
| 3 | Male; 59 years old | Patient suffering from diabetes mellitus complained of insomnia for few weeks. He was given the herbal composition at 2 capsules nightly and responded at follow-up in one month. He was maintained on the same until now. There were no complaints of heatiness. |
| 4 | Female; 66 years old | Patient suffered from insomnia after recovering from stroke for a few weeks. She was given the herbal composition at 2 capsules nightly and responded in 8 days. She was maintained on the same until now. There were no complains of heatiness. |
| 5 | Female; 20 years old | Patient suffering from anxiety complained of insomnia for one month. She was given the herbal composition at 2 capsules nightly and responded in 5 days. After 10 months, she was able to sleep naturally and did not require the herbal composition anymore. There were no complaints of heatiness. |

In this study, the herbal composition taken by the patients were based on the composition listed in Table 2.

In short, as shown in Table 4, in all of the five patients administrated with herbal composition, the symptoms of insomnia and anxiety were greatly alleviated without any complaints on heatiness.

Example 6

Pretreatment of Herbs

Before being used in the preparation for the herbal composition in accordance with the present invention, each of the herbs as listed in Table 2 was pretreated according to the corresponding procedure as follows.

TABLE 5

| No. | Herb | Pre-treatment procedures |
|---|---|---|
| 1 | Radix Rehmanniae | Take Radix Rehmanniae, clean and remove foreign matters thereon, gently heat it to about 80% dry, let cool and cut into pieces. |
| 2 | Poria | Take Poria, immerse, clean, moisten and steam slightly, cut it into thick pieces, and dry under the sun. |
| 3 | Ganoderma Lucidum | Take Ganoderma Lucidum, remove foreign matters thereon, wash off mud and sands, drain off water, steam with circulating vapor for 1 hour, take out, dry by baking or under the sun, and grind to the coarsest powder. |
| 4 | Semen Ziziphi Spinosae | Take Semen Ziziphi Spinosae and remove putamina and foreign matters thereon. Put the cleaned medicinal material into a hot pot, use gentle heat to fry till it swells up and the color darkens slightly, pound into pieces upon using. |
| 5 | Semen Platycladi | Take Semen Platycladi and remove foreign matters thereon, residual spikes and skins. Put the clean medicinal material into the hot pot, use gentle heat to fry till the surface color becomes yellow with a special odor, take out and let cool. |
| 6 | Radix Rehmanniae Praeparata | Take clean dried Rehmanniae root, add yellow wine and mix well, cover to moisten thoroughly, steam in high pressure cabinet at 115° C. for 2.5 hours, and then use the interlayer to heat and steam at 110° C. for 1.5 hours, take out and dry under the sun to 80% dry. Use the yellow wine to moisten and re-steam one more time using the same method, take out and dry under the sun to 80% dry, cut into thick pieces, and dry under the sun. Use 20 kg yellow wine per 100 kg dried Rehmanniae root. |
| 7 | Radix Angelicae Sinensis | Take Radix Angelicae Sinensis, remove foreign matters thereon, clean, moisten thoroughly, cut into thin pieces, and dry at a temperature less than 60° C. Take cleaned Radix Angelicae Sinensis pieces, add wine and mix well, cover to moisten for about 4 hours, use gentle heat to fry till the surface color becomes deep yellow with a few burned spots, take out and let cool. |

TABLE 5-continued

| No. | Herb | Pre-treatment procedures |
|---|---|---|
| 8 | Radix Et Rhizoma Salviae Miltiorrhizae | Take Radix Et Rhizoma Salviae Miltiorrhizae, remove foreign matters thereon and residual stalks, wash off mud and sands, moisten thoroughly, cut into pieces, and dry. |
| 9 | Rhizoma Chuanxiong | Take Rhizoma Chuanxiong, remove foreign matters thereon, separate large and small ones, clean, soak in water till the husk becomes soft, take out, moisten thoroughly, cut into thin pieces, and dry. |
| 10 | Rhizoma Atractylodis Macrocephalae | Take Rhizoma Atractylodis Macrocephalae, remove foreign matters thereon, clean, moisten thoroughly, cut into thick pieces, and dry. Use high heat to heat up a cleaned pot, sprinkle wheat bran; when the smoke emerges, put the clean medicinal material into the heated pot, stir constantly and control the heat appropriately, fry till the surface of the medicinal material shows toast tan color with a smell of scorched scent, take out, sift out wheat bran, and let cool. Use 10 kg wheat bran per 100 kg Rhizoma Atractylodis Macrocephalae pieces. |
| 11 | Fructus Gardeniae | Take Fructus Gardeniae and remove foreign matters thereon. Put the clean medicinal material into a hot pot, use gentle heat to fry till the color becomes tawny, take out, sift out the ash and let cool. |
| 12 | Cortex Moutan | Take Cortex Moutan, remove foreign matters thereon, clean, and dry under the sun. |
| 13 | Radix Bupleuri | Take Radix Bupleuri, remove foreign matters thereon and residual stalks, clean, moisten thoroughly, cut into thick pieces, and dry. Take Radix Bupleuri pieces, add vinegar and mix well, cover slightly, use gentle heat to fry till dry, take out and let cool. Use 10 kg vinegar per 100 kg Radix Bupleuri. |
| 14 | Radix Paeoniae Alba | Take Radix Paeoniae Alba, clean, moisten thoroughly, cut into thin pieces, and dry. Take Radix Paeoniae Alba pieces, use wine to mix well, cover slightly, use gentle heat to fry till the color becomes faint yellow upon complete absorption of wine, take out, and let cool. |
| 15 | Rhizoma Cyperi | Take Rhizoma Cyperi and remove hair and foreign matters thereon. Take Rhizoma Cyperi particles, add vinegar to mix well, cover to moisten overnight, fry till the color becomes faint yellow, take out and let cool. Use 20 kg vinegar and 20 kg water per 100 kg Rhizoma Cyperi. |
| 16 | Pericarpium Citri Reticulatae | Take Pericarpium Citri Reticulatae, brush off clay, and remove all foreign matters thereon. |
| 17 | Fructus Aurantii | Take Fructus Aurantii, remove foreign matters thereon, clean it, moisten thoroughly, cut into thin pieces, dry, sift out sloughed pulp and kernel, heat clean pot, and sprinkle wheat bran. When the smoke emerges, add Fructus Aurantii pieces, stir constantly, fry till the color becomes faint yellow, take out, sift out wheat bran, and let cool. Use 10~15 kg wheat bran per 100 kg Fructus Aurantii. |
| 18 | Radix Glycyrrhizae | Take Radix Glycyrrhizae, remove foreign matters thereon, clean, moisten thoroughly, cut into thick pieces, and dry. |
| 19 | Os Draconis | Take Os Draconis, brush off clay; take cleaned Os Draconis and break into pieces, load to a fire-retardant container and heat under high heat till they become red thoroughly, take out, let cool, and crush them into pieces. |

Example 7

Anti-Depressant and Anti-Anxiety Activity

The following three tests on mice were conducted to investigate the anti-depressant and anti-anxiety activities of the herbal composition of the present invention.

In all these tests, the test item was the herbal composition as described in Table 2 in the form of a powder. The reference item was Imipramine hydrochloride manufactured by Sigma-Aldrich, USA (for forced swimming and tail suspension tests), and Diazepam tablets supplied by Tianjin Lisheng Pharmaceutical Co. Ltd, China (for elevated plus maze test).

Male mice weighing 18-22 g at the start of the study were obtained from the Guangdong Medical Laboratory Animal Center, China.

At the beginning of each test, the test item was administrated at three dose levels of 69, 208, and 624 mg per kg of mouse by oral route (gastric gavage). For the Forced Swimming Test and Tail Suspension Test, Imipramine was administrated at the dose level of 20 mg per kg of mouse by oral route (gastric gavage), whereas Diazepam was administrated at the dose level of 2 mg per kg of mouse by oral route (gastric gavage). The Control group only received physiological saline orally by gastric gavage.

Forced Swimming Test

A depressed state can be induced in mice by forcing them to swim in an enclosed water tank from which they cannot escape. After an initial period of vigorous activity, the mice adopt a characteristic immobile posture which is readily identifiable. Typically, mice previously administrated with anti-depressant treatments would experience a reduced time of immobility.

In this test, two batches of mice were used and in each batch, the mice were allotted at random to five groups, each consisting of ten animals. The results of the test were shown in Tables 6-1 and 6-2 below.

TABLE 6-1

(First Batch)

| Treatment | Dose (mg/kg) | Time of immobility (s) |
| --- | --- | --- |
| Control | — | 93.19 ± 31.07 |
| Herbal Composition (Low) | 69 | 67.91 ± 21.84 |
| Herbal Composition (Medium) | 208 | 55.14 ± 23.26** |
| Herbal Composition (High) | 624 | 54.35 ± 7.15** |
| Imipramine | 20 | 43.92 ± 17.63** | as compared with the Control group:
*$p < 0.05$;
**$p < 0.01$

TABLE 6-2

(Second Batch)

| Treatment | Dose (mg/kg) | Time of immobility (s) |
| --- | --- | --- |
| Control | — | 110.61 ± 28.03 |
| Herbal Composition (Low) | 69 | 80.00 ± 33.04* |
| Herbal Composition (Medium) | 208 | 72.32 ± 25.64** |
| Herbal Composition (High) | 624 | 73.89 ± 20.21* |
| Imipramine | 20 | 59.90 ± 17.40** | as compared with the Control group:
*$p < 0.05$;
**$p < 0.01$

The results showed that for both batches, there was a reduction in the immobility time for mice administrated with the herbal composition in all three dosage groups.

Tail Suspension Test

When a mouse is suspended by its tail, its basic instinct first drives him to struggle, but this inescapable stress will eventually force it to develop an immobile posture. This immobility will then be taken as an index of its depressive state which in turn parallels its behavioral despair. Researchers found that duration of immobility would be reduced in mice administrated with antidepressants.

In this test, two batches of mice were used and in each batch, the mice were allotted at random to five groups, each consisting of ten animals. The results of the test were shown in Tables 7-1 and 7-2 below.

TABLE 7-1

(First Batch)

| Treatment | Dose (mg/kg) | Time of immobility (s) |
| --- | --- | --- |
| Control | — | 115.89 ± 39.27 |
| Herbal Composition (Low) | 69 | 83.57 ± 39.66 |
| Herbal Composition (Medium) | 208 | 71.57 ± 21.03** |
| Herbal Composition (High) | 624 | 73.19 ± 23.56** |
| Imipramine | 20 | 60.08 ± 16.67** | as compared with the Control group: *$p < 0.05$; **$p < 0.01$

TABLE 7-2

(Second Batch)

| Treatment | Dose (mg/kg) | Time of immobility (s) |
| --- | --- | --- |
| Control | — | 100.76 ± 33.49 |
| Herbal Composition (Low) | 69 | 75.96 ± 39.66 |
| Herbal Composition (Medium) | 208 | 68.167 ± 19.43* |
| Herbal Composition (High) | 624 | 69.71 ± 23.59* |
| Imipramine | 20 | 52.66 ± 17.05** | as compared with the Control group: *$p < 0.05$; **$p < 0.01$

It can be shown from the results that the mice administrated with the herbal composition in all dosage groups experienced reduced immobility time. Also, the medium dosage group (208 mg/kg) showed the biggest reduction of immobility time.

Elevated Plus Maze Test

In this common test for assessing anxiety, the mouse is initially placed in the center of an elevated plus-shaped maze consisting of 4 arms (2 open arms & 2 enclosed arms), with its head facing one of the two open arms. The basic measure is to determine the unconditioned response of the tested mouse to a potentially dangerous environment and the preference of the tested mouse for dark, enclosed places over bright places, and exposed places. Typically, the tested mice would avoid entering into open arms due to anxiety, and mice administrated with anxiolytic and anxiogenic treatments would have decreased aversion to heights and open spaces.

In this test, two batches of mice were used and in each batch, the mice were allotted at random to five groups, each consisting of ten animals. The results of the test were shown in Tables 8-1 and 8-2 below.

TABLE 8-1

(First Batch)

| Treatment | Dose (mg/kg) | Ratio of open arms entry (%) | Ratio of time spent in open arms (%) | Head dipping (times) |
|---|---|---|---|---|
| Control | — | 36.16 ± 6.13 | 31.94 ± 10.82 | 16.2 ± 4.61 |
| Herbal Composition (Low) | 69 | 43.96 ± 9.10* | 41.48 ± 11.25** | 19.0 ± 7.04 |
| Herbal Composition (Medium) | 208 | 47.61 ± 12.19* | 54.82 ± 23.89* | 21.3 ± 9.15 |
| Herbal Composition (High) | 624 | 48.49 ± 8.21** | 45.31 ± 7.23** | 19.3 ± 5.23 |
| Diazepam | 2 | 51.27 ± 10.08 | 50.51 ± 10.58 | 20.67 ± 10.42 | as compared with the Control group:
*$p < 0.05$;
**$p < 0.01$

TABLE 8-2

(Second Batch)

| Treatment | Dose (mg/kg) | Ratio of open arms entry (%) | Ratio of time spent in open arms (%) | Head dipping (times) |
|---|---|---|---|---|
| Control | — | 33.66 ± 7.95 | 29.82 ± 8.88 | 14.0 ± 4.64 |
| Herbal Composition (Low) | 69 | 46.33 ± 14.18* | 37.99 ± 7.63* | 17.8 ± 5.67 |
| Herbal Composition (Medium) | 208 | 52.97 ± 11.22** | 42.21 ± 6.91** | 19.8 ± 6.01* |
| Herbal Composition (High) | 624 | 48.61 ± 7.40** | 41.33 ± 7.96** | 19.7 ± 6.24* |
| Diazepam | 2 | 52.48 ± 9.97 | 47.52 ± 12.35 | 21.5 ± 6.15** | as compared with the Control group:
*$p < 0.05$;
**$p < 0.01$

The ratio of open arm entry is the frequency of the times the mice entering the open arms to the total frequency of entry into both open and enclosed arms (in percentages). Likewise, the ratio of time spent in open arms is the proportion of time spent by the mice in the open arms to the total times spent in both open and enclosed arms (in percentages).

As shown in the results, mice administrated with the herbal composition in all three dosage groups made more open arm visits, spent longer in the open arms and had more head dippings as compared to those in the control group. This showed that the herbal composition exhibited anti-anxiety activity in the mice administrated thereof.

CONCLUSION

From the forced swimming and tail suspension tests, under the experimental conditions described above, antidepressant activity of the herbal composition in accordance with the present invention was observed at all three doses. Doses that may be used include but not limited to 200 to 250 mg/kg.

Anti-anxiety activity of the herbal composition in accordance with the present invention was observed at the dose range shown above.

The preferred embodiments of the present invention as well as various examples thereof, are thus fully described. Although the description referred to particular embodiments, it will be clear to one skilled in the art that the present invention may be practiced with variation of these specific details. Hence this invention should not be construed as limited to the embodiments set forth herein.

For example, this composition may be taken orally in different forms such as powder, capsule, liquid, or mixed with milk powder. Starch may be used as a pharmaceutical carrier for the composition but it is clear that other carrier can also be employed.

What is claimed is:

1. An herbal composition for treating insomnia or anxiety in a mammal in need thereof comprising a mixture of:
   i.) an effective amount of a purified, ethanol precipitated water extract of *Radix Rehmanniae*; and
   ii.) an effective amount of a mixed-filtrate extract, wherein the mixed-filtrate extract is a hot water extract of *Os Draconis* combined with an ethanol extract of: *Poria; Ganoderma Lucidum; Semen Ziziphi Spinosae; Semen Platycladi; Radix Rehmanniae Preparata; Radix Angelicae Sinensis; Radix Et Rhizoma Salviae Miltiorrhizae; Rhizoma Chuanxiong; Rhizoma Atractylodis Macrocephalae; Fructus Gardeniae; Cortex Moutan; Radix Bupleuri; Radix Paeoniae Alba; Rhizoma Cyperi; Pericarpium Citri Reticulatae; Fructus Aurantii* and *Radix Giycyrrhizae*; wherein said herbal composition is formulated for oral administration to reduce or inhibit insomnia or anxiety in said mammal.

2. The herbal composition of claim 1 further comprising a pharmaceutically acceptable carrier or vehicle.

3. The herbal composition of claim 2, wherein said herbal composition is provided in a powder form or an incapsulated form.

4. The herbal composition of claim 2, wherein said herbal composition comprises
   a) about 5 weight percent to about 15 weight percent said *Radix Rehmanniae*;

b) about 3 weight percent to about 10 weight percent said *Poria;*
c) about 3 weight percent to about 10 weight percent said *Ganoderma Lucidum;*
d) about 2 weight percent to about 8 weight percent said *Semen Ziziphi Spinosae;*
e) about 2 weight percent to about 8 weight percent said *Semen Platycladi;*
f) about 2 weight percent to about 8 weight percent said *Radix Rehmanniae Praeparata;*
g) about 2 weight percent to about 8 weight percent said *Radix Angelicae Sinensis;*
h) about 2 weight percent to about 8 weight percent said *Radix Et Rhizoma Salviae Miltiorrhizae;*
about 1 weight percent to about 5 weight percent said *Rhizoma Chuanxiong;*
j) about 1 weight percent to about 5 weight percent said *Rhizome Atractylodis Macrocephalae;*
k) about 1 weight percent to about 6 weight percent said *Fructus Gardeniae;*
l) about 2 weight percent to about 8 weight percent said *Cortex Moutan;*
m) about 1 weight percent to about 6 weight percent said *Radix Bupleuri;*
n) about 2 weight percent to about 8 weight percent said *Radix Paeoniae Alba;*
o) about 2 weight percent to about 8 weight percent said *Rhizoma Cyperi;*
p) about 1 weight percent to about 6 weight percent said *Pericarpium Citri Reticulatae;*
q) about 2 weight percent to about 8 weight percent said *Fructus Aurantii;*
r) about 1 weight percent to about 6 weight percent said *Radix Glycyrrhizae;*
s) about 3 weight percent to about 10 weight percent said *Os Draconis*; and
t) about 5 weight percent to about 15 weight percent said carrier.

5. The herbal composition of claim 4, wherein said herbal composition is water soluble.

6. The herbal composition of claim 4, wherein said herbal composition comprises
a) about 9 weight percent to about 12 weight percent said *Radix Rehmanniae;*
b) about 4 weight percent to about 8 weight percent said *Poria;*
c) about 4 weight percent to about 8 weight percent said *Ganoderma Lucidum;*
d) about 3 weight percent to about 6 weight percent said *Semen Ziziphi Spinosae;*
e) about 3 weight percent to about 6 weight percent said *Semen Platycladi;*
f) about 3 weight percent to about 6 weight percent said *Radix Rehmanniae Praeparata;*
g) about 3 weight percent to about 6 weight percent said *Radix Angelicae Sinensis;*
h) about 3 weight percent to about 6 weight percent said *Radix Et Rhizome Salviae Miltiorrhizae;*
i) about 1 weight percent to about 4 weight percent said *Rhizome Chuanxiong;*
j) about 1 weight percent to about 4 weight percent said *Rhizoma Atractylodis Macrocephalae;*
k) about 2 weight percent to about 5 weight percent said *Fructus Gardeniae;*
l) about 3 weight percent to about 6 weight percent said *Cortex Moutan;*
m) about 2 weight percent to about 5 weight percent said *Radix Bupleuri;*
n) about 3 weight percent to about 6 weight percent said *Radix Paeoniae Alba;*
o) about 3 weight percent to about 6 weight percent said *Rhizome Cyperi;*
p) about 2 weight percent to about 5 weight percent said *Pericarpium Citri Reticulatae;*
q) about 3 weight percent to about 6 weight percent said *Fructus Aurantii;*
r) about 2 weight percent to about 5 weight percent said *Radix Glycyrrhizae;*
s) about 4 weight percent to about 8 weight percent said *Os Draconis*; and
t) about 9 weight percent to about 12 weight percent said carrier.

7. The herbal composition of claim 6, wherein said herbal composition is water soluble.

8. The herbal composition of claim 6, wherein said herbal composition comprises
a) about 10 weight percent said *Radix Rehmanniae;*
b) about 5 weight percent said *Poria;*
c) about 5 weight percent said *Ganoderma Lucidum;*
d) about 5 weight percent said *Semen Ziziphi Spinosae;*
e) about 5 weight percent said *Semen Platycladi;*
f) about 5 weight percent said *Radix Rehmanniae Praeparata;*
g) about 5 weight percent said *Radix Angelicae Sinensis;*
h) about 5 weight percent said *Radix Et Rhizome Salviae Miltiorrhizae;*
i) about 2 weight percent said *Rhizome Chuanxiong;*
j) about 2 weight percent said *Rhizoma Atractylodis Macrocephalae;*
k) about 4 weight percent said *Fructus Gardeniae;*
l) about 5 weight percent said *Cortex Moutan;*
m) about 4 weight percent said *Radix Bupleuri;*
n) about 5 weight percent said *Radix Paeoniae Alba;*
o) about 5 weight percent said *Rhizome Cyperi;*
p) about 4 weight percent said *Pericarpium Citri Reticulatae;*
q) about 5 weight percent said *Fructus Aurantii;*
r) about 4 weight percent said *Radix Glycyrrhizae;*
s) about 5 weight percent said *Os Draconis*; and
t) about 10 weight percent said carrier.

9. The herbal composition of claim 8, wherein said herbal composition is water soluble.

10. A method of preparing the herbal composition of claim 1 further comprising the step of:
    iv) mixing the herbal composition with a pharmaceutical carrier and packaging.

11. The herbal composition of claim 1, wherein said herbal composition is obtained by:
    i.) preparing the purified, ethanol precipitated water extract of *Radix Rehmannia* by:
    a) soaking *Radix Rehmanniae* powders in water to provide an water extract of *Radix Rehmanniae;*
    b.) simmering, extracting and filtering the water extract of *Radix Rehmanniae* to obtain a first *Radix Rehmanniae* filtrate and a *Radix Rehmanniae* residue;
    c.) heating the *Radix Rehmanniae* residue in water, simmering and extracting to provide a second *Radix Rehmanniae* filtrate;
    d.) combining the first *Radix Rehmanniae* filtrate with the second *Radix Rehmanniae* filtrate to provide a combined filtrate, concentrating the combined filtrate and purifying the concentrated filtrate by ethanol precipitation and filtering to provide a purified filtrate and purified residue;

e) concentrating the purified filtrate under reduced pressure, and dried to provide the purified, ethanol precipitated water extract of *Radix Rehmanniae;* ii.) preparing the mixed-filtrate extract by:

a) heating *Os Draconis* powders with water, cooling to room temperature and filtering to obtain an *Os Draconis* filtrate and an *Os Draconis* residue;

b) extracting *Poria, Ganoderma* . . . and *Radix Glycyrrhizae* with ethanol to provide an ethanol mixture, heating the resulting ethanol mixture, extracting and filtering the ethanol mixture to provide an herb filtrate and an herb residue;

c) combining the *Os Draconis* residue with the herb residue to provide a mixed-residue, extracting the mixed-residue with heated water by steam to provide a mixed-residue extract;

d) combining the *Os Draconis* filtrate, the herb filtrate and the mixed-residue extract to provide a mixed-filtrate, concentrating the mixed-filtrate to provide a mixed-filtrate paste and drying the mixed-filtrate paste to provide the mixed-filtrate extract; and iii) combining the purified, ethanol precipitated water extract of *Radix Rehmannia* with mixed-filtrate extract to provide the herbal composition.

12. A method of preparing the herbal composition of claim 1 comprising:

i.) preparing the purified, ethanol precipitated water extract of *Radix Rehmannia* by:

a) soaking *Radix Rehmanniae* powders in water to provide an water extract of *Radix Rehmanniae;* b.) simmering, extracting and filtering the water extract of *Radix Rehmanniae* to obtain a first *Radix Rehmanniae* filtrate and a *Radix Rehmanniae* residue;

c.) heating the *Radix Rehmanniae* residue in water, simmering and extracting to provide a second *Radix Rehmanniae* filtrate;

d.) combining the first *Radix Rehmanniae* filtrate with the second *Radix Rehmanniae* filtrate to provide a combined filtrate, concentrating the combined filtrate and purifying the concentrated filtrate by ethanol precipitation and filtering to provide a purified filtrate and purified residue;

e) concentrating the purified filtrate under reduced pressure, and dried to provide the purified, ethanol precipitated water extract of *Radix Rehmanniae;* ii.) preparing the mixed-filtrate extract by:

a) heating *Os Draconis* powders with water, cooling to room temperature and filtering to obtain an *Os Draconis* filtrate and an *Os Draconis* residue;

b) extracting *Poria, Ganoderma* . . . and *Radix Glycyrrhizae* with ethanol to provide an ethanol mixture, heating the resulting ethanol mixture, extracting and filtering the ethanol mixture to provide an herb filtrate and an herb residue;

c) combining the *Os Draconis* residue with the herb residue to provide a mixed-residue, extracting the mixed-residue with heated water by steam to provide a mixed-residue extract;

d) combining the *Os Draconis* filtrate, the herb filtrate and the mixed-residue extract to provide a mixed-filtrate, concentrating the mixed-filtrate to provide a mixed-filtrate paste and drying the mixed-filtrate paste to provide the mixed-filtrate extract; and iii) combining the purified, ethanol precipitated water extract of *Radix Rehmannia* with the mixed-filtrate extract to provide the herbal composition.

13. The method of claim 10, wherein said pharmaceutical carrier is starch.

14. A method of treating insomnia or anxiety in a mammal in need thereof comprising administering to said mammal an effective amount of the herbal composition of claim 1.

15. A method of treating insomnia or anxiety in a mammal in need thereof comprising administering to said mammal an effective amount of the herbal composition of claim 4.

16. A method of treating insomnia or anxiety in a mammal in need thereof comprising administering to said mammal an effective amount of the herbal composition of claim 6.

17. A method of treating insomnia or anxiety in a mammal in need thereof comprising administering to said mammal an effective amount of the herbal composition of claim 8.

* * * * *